US009588583B2

United States Patent
Lightcap et al.

(10) Patent No.: US 9,588,583 B2
(45) Date of Patent: Mar. 7, 2017

(54) SYSTEM AND METHOD FOR PROVIDING SUBSTANTIALLY STABLE HAPTICS

(75) Inventors: Christopher Alan Lightcap, Davie, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 247 days.

(21) Appl. No.: 13/339,369

(22) Filed: Dec. 28, 2011

(65) Prior Publication Data

US 2012/0176306 A1    Jul. 12, 2012

Related U.S. Application Data

(60) Provisional application No. 61/428,210, filed on Dec. 29, 2010.

(51) Int. Cl.
*G06F 3/01*    (2006.01)
*G09B 23/28*    (2006.01)

(52) U.S. Cl.
CPC .............. *G06F 3/016* (2013.01); *A61B 34/76* (2016.02); *G09B 23/28* (2013.01); *A61B 34/20* (2016.02)

(58) Field of Classification Search
CPC ........ G06F 3/016; G06F 2203/012–2203/015; G06F 3/01; G06T 15/08; G06T 15/10; G06T 17/05; G06T 17/10; A61B 2019/2292; A61B 34/20; A61B 34/76; A61B 34/77; G09B 23/28; A61F 4/00
See application file for complete search history.

(56) References Cited

U.S. PATENT DOCUMENTS

| 7,084,867 | B1 | 8/2006 | Ho et al. |
| 7,206,626 | B2 * | 4/2007 | Quaid, III ..................... 600/407 |
| 7,864,173 | B2 * | 1/2011 | Handley et al. .............. 345/420 |
| 7,916,121 | B2 * | 3/2011 | Braun et al. .................. 345/156 |
| 8,571,628 | B2 * | 10/2013 | Kang ..................... A61N 1/372 600/407 |
| 2004/0024311 | A1 * | 2/2004 | Quaid, III .............. A61B 34/20 600/428 |
| 2004/0106916 | A1 * | 6/2004 | Quaid .................... A61B 34/20 606/1 |

(Continued)

FOREIGN PATENT DOCUMENTS

| CN | 101031236 A | 9/2007 |
| CN | 101815981 A | 8/2010 |
| WO | WO-2005/009215 A2 | 2/2005 |

OTHER PUBLICATIONS

Kim et al., "Haptic Interaction and Volume Modeling Techniques for Realistic Dental Simulation," *Visual Comput., Intern. Journ. of Computer Graphics*, vol. 22, pp. 90-98 (2006).

(Continued)

*Primary Examiner* — Jennifer Mehmood
*Assistant Examiner* — Sardis F Azongha
(74) *Attorney, Agent, or Firm* — Foley & Lardner LLP

(57) ABSTRACT

A system for providing substantially stable haptics includes at least one computer configured to identify a first subset and a second subset of haptic interaction geometric primitives for a virtual tool. The computer is configured to determine based on the first subset, haptic forces in a first subspace. The computer is also configured to determine based on the second subset, haptic forces in a second subspace different from the first subspace.

24 Claims, 5 Drawing Sheets

(56) References Cited

U.S. PATENT DOCUMENTS

2006/0142657 A1* 6/2006 Quaid ................ A61N 1/372
   600/424
2008/0004633 A1* 1/2008 Arata ................ A61B 19/5244
   606/130
2009/0012532 A1 1/2009 Quaid et al.

OTHER PUBLICATIONS

Petersik et al., "Realistic Haptic Interaction in Volume Sculpting for Surgery Simulation," *Surgery Simulation and Soft Tissue Modeling*, vol. 2673, pp. 194-202 (2003).

Ahmadi et al., "Non-Hertzian Contact Stress Analysis for an Elastic Half-Space Normal and Sliding Contact," *Int. J. Solids Structures*, vol. 19, No. 4, pp. 357-373 (1983).

Bei et al., "Multibody Dynamic Simulation of Knee Contact Mechanics," *Medical Engineering & Physics*, vol. 26, pp. 777-789 (2004).

International Search Report and Written Opinion issued in related International Patent Application No. PCT/US2011/067202, completed Apr. 24, 2012.

\* cited by examiner

SYSTEM AND METHOD FOR PROVIDING SUBSTANTIALLY STABLE HAPTICS

This application claims the benefit of priority under 35 U.S.C. §119(e) of U.S. Provisional Application No. 61/428,210, filed Dec. 29, 2010, which is incorporated by reference herein in its entirety.

BACKGROUND OF THE INVENTION

Field of the Invention

The invention relates generally to the field of haptics. Specifically, the invention relates to a system and method for providing substantially stable haptics in a system using a virtual tool.

Description of Related Art

The field of haptics relates to, among other things, human interactive devices that provide tactile and/or force feedback to a user to achieve a desired goal. Tactile feedback may include providing a user with tactile sensations such as, for example, vibration. Force feedback may include providing various forms of force to a user, such as a positive force or a resistance to movement.

A common use of haptics is to provide a user of a device with guidance or limits for manipulation of that device. For example, the device may be a robotic system having an object, such as a physical tool, for performing a specified function. The user's manipulation of the physical tool can be guided or limited through the use of haptics to provide feedback to the user during manipulation of the physical tool.

Often such guidance is provided by using a computer to create a virtual environment that effectively guides or limits manipulation of the physical tool. The computer may create an association between the physical tool and a virtual tool (a virtual representation of the physical tool) in the virtual environment. The computer also may construct a haptic object within the virtual environment. The haptic object may provide boundaries for guiding or limiting movement of the virtual tool. For example, when the virtual tool interacts with a boundary of the haptic object, tactile or force feedback may be provided to the user. The guidance or limitation resulting from the interaction between the virtual tool and the haptic object effectively provides guidance or limitation for the user's manipulation of the physical tool.

A specific example of such a robotic system using haptics can be found in computer-assisted surgical systems. In such systems, a physical tool, such as a bone-cutting tool, may be associated with a virtual tool in a virtual environment. A pre-operative surgical plan may be used to identify a region for bone resection, which will then be used to create a haptic object in the virtual environment. For example, the haptic object may represent the boundaries of the bone-resection region. The surgeon will receive tactile or force feedback when the virtual tool interacts with the boundaries of the haptic object. This feedback can assist the surgeon in maintaining the bone-cutting tool with the bone-resection region, according to his/her pre-operative plan.

Feedback is generated based on the interaction of the virtual tool with the haptic object. A fundamental relationship often established for haptics is a linear elastic spring, where the contact force applied by the haptic object may be defined by the spring constant, K, and the displacement into the haptic object, Δx, such that $$\vec{f} = K \Delta \vec{x}$$

To determine the appropriate feedback, the computer is usually able to determine the interaction between the virtual tool and the haptic object. This interaction is often determined by identifying a single haptic interaction point (HIP) that will represent the location of the virtual tool. For example, a HIP may be defined as the center of a spherical cutting tool, as long as the haptic object is offset from a resection depth by the radius of the tool. In such cases, the computer uses the relationship between the HIP and the haptic object to determine the interaction of the virtual tool with the haptic object.

In certain circumstances, a single HIP may not be fully effective for determining the interaction between the virtual tool and the haptic object. For example, an irregular-shaped virtual tool may not be adequately represented by a single HIP. Due to the irregular shape of the virtual tool, a single HIP may not adequately account for variations on the cutting surface of the tool and/or rotation of the tool. In this case, multiple HIPs may be defined along the contour of the virtual tool. For example, as shown in FIG. 2, three HIPs 20 (points 1, 2, and 3) may be defined on the outer edge of a virtual tool 10 to provide a better estimation of the interaction between the virtual tool and the haptic object.

Even multiple HIPs may not be fully effective for determining the interaction between the virtual tool and the haptic object. For example, traditional multi-point haptic forces may not be stable because of the competing forces that exist along a bi-lateral constraint such as a plane or line. In the example illustrated in FIG. 2, the irregular-shaped virtual tool 10 has outer HIPs (points 1 and 3) and an inner HIP (point 2). The outer HIPs are in an antagonistic relationship, such that haptic forces determined from the interaction of those outer HIPs (points 1 and 3) with the boundary 40 of the haptic object are in opposite directions, leading to an undesirable oscillation about a haptic plane. This unstable behavior can be attributed to measurement noise, discretization errors, and the competing forces between contact points.

In view of the foregoing, a need exists for a system and method that can provide substantially stable haptics for a haptic object that will correct undesirable oscillation caused by behavior such as measurement noise, discretization errors, and competing forces between interaction/contact points.

SUMMARY

According to an aspect of the present invention, a system for providing substantially stable haptics is provided. The system includes at least one computer configured to identify a first subset and a second subset of haptic interaction geometric primitives for a virtual tool, determine based on the first subset, haptic forces in a first subspace, and determine based on the second subset, haptic forces in a second subspace different from the first subspace.

According to another aspect of the present invention, a method for providing substantially stable haptics is provided. The method includes the steps of identifying a first subset and a second subset of haptic interaction geometric primitives for a haptic object, determining based on the first subset, by at least one computer, haptic forces for a first subspace, and determining based on the second subset, by at least one computer, haptic forces in a second subspace different from the first subspace.

BRIEF DESCRIPTION OF THE DRAWINGS

The accompanying drawings, which are incorporated in and constitute a part of this specification, illustrate embodi

Figure 1:
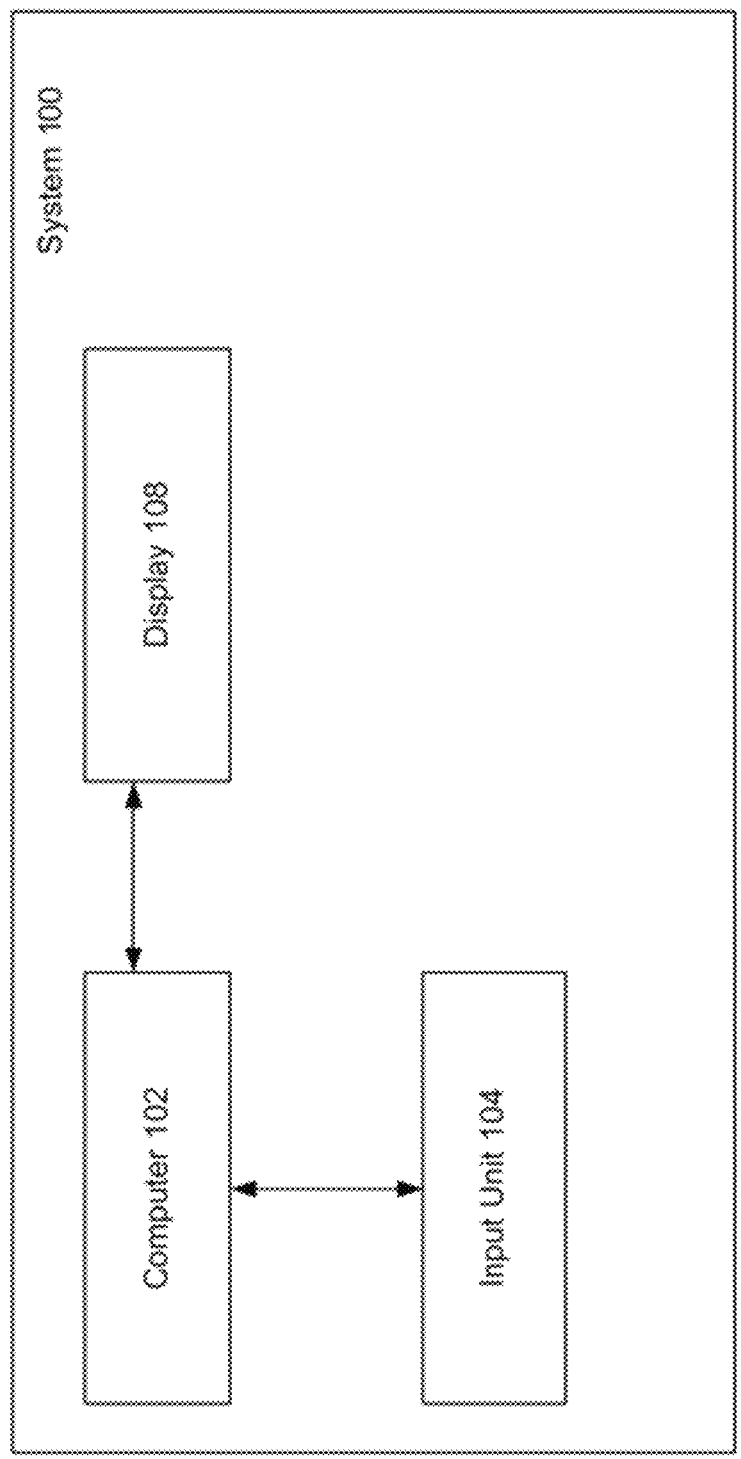
- FIG. 1 is a block diagram of a system for providing substantially stable haptics according to the present invention.

DETAILED DESCRIPTION OF THE
PREFERRED EMBODIMENTS

Presently preferred embodiments of the invention are illustrated in the drawings. An effort has been made to use the same or like reference numbers throughout the drawings to refer to the same or like parts.

Overview

The present invention relates to a system and method for providing substantially stable haptics. According to the present invention, a computer can be used to identify multiple haptic interaction geometric primitives (HIGP) for a virtual tool. To overcome one or more problems in conventional systems, the present invention identifies subsets of the HIGPs and determines haptic forces in subspaces corresponding to those subsets. Those haptic forces may then be used to determine a total haptic interaction force.

In general, a subspace is a set of vectors that is closed under addition and scalar multiplication. For example, geometrically, a subspace of $R^n$ can be a flat through the origin, i.e., a copy of a lower dimensional (or equi-dimensional) Euclidean space sitting in n dimensions. For example, in three-dimensional space $R^3$ there are types of subspaces that can be viewed as different from one another (even though they may overlap), including, without limiting:

(a) lines within $R^3$, which are one-dimensional subspaces of $R^3$;

(b) planes within $R^3$, which are two-dimensional subspaces of $R^3$; and (c) the entire set $R^3$, which is a three-dimensional subspace of itself.

In n-dimensional space $R^n$, there are subspaces of every dimension from 0 to n.

Embodiment of a System for Providing Substantially Stable Haptics

FIG. 1 is a block diagram of an embodiment of a computer-assisted system 100 for providing substantially stable haptics. The system includes a computer 102, which is in communication with an input unit 104 and a display 108.

In general, the computer 102 may be configured to determine haptic force(s) based on a virtual tool and, preferably, based on the interaction between a virtual tool and a haptic object. The computer 104 may be configured to, among other things, associate a physical tool with the virtual tool, identify HIGPs for the virtual tool, create the haptic object or objects, determine the interaction between the virtual tool and the haptic object, determine feedback to be provided to the user, and/or control the feedback provided to the user.

The computer 102 may be any known computing system but is preferably a programmable, processor-based system. For example, the computer 102 may include a microprocessor, a hard drive, random access memory (RAM), read only memory (ROM), input/output (I/O) circuitry, and any other well-known computer component. The computer 102 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 102 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The input unit 104 enables information to be communicated to the system 100, including the computer 102. The input unit 104 may be one or more devices used for communication of information, such as features of the virtual tool, features of the haptic object, the location of the physical tool, and/or the location of the workpiece upon which the physical tool is or will be working.

The input unit 104 is connected to the computer 102 and may include any device(s) enabling input to a computer. As specific examples, the input unit 104 can include a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. The input unit 104 may also include surgical navigation equipment that provides data to the computer 102. For example, the input unit 104 can include a tracking system for tracking the position of surgical tools and patient anatomy. The tracking system may be, for example, an optical, electromagnetic, radio, acoustic, mechanical, or fiber optic tracking system.

The display 108 is a visual interface between the system 100 and the user. The display 108 enables information to be communicated from the system 100, including the computer 102, to the user. The display 108 may be one or more devices used for communication of information, such as features of the virtual tool, features of the haptic object, and/or the location of the virtual tool relative to the haptic object. In some embodiments, the display 108 displays graphical representations of virtual tools and haptic objects in a virtual environment.

The display 108 is connected to the computer 102 and may be any device suitable for displaying text, images, graphics, and/or other visual output. For example, the display 108 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display 108 may be disposed on or near the computer 102 (e.g., mounted within a cabinet also comprising the computer 102) or may be remote from the computer 102 (e.g., mounted on a wall of an operating room or other location suitable for viewing by the user). The display 108 is preferably adjustable so that the user can position/reposition the display 108 as needed during a surgical procedure. For example, the display 108 may be disposed on an adjustable arm (not shown) or on any other location well-suited for ease of viewing by the user. The display 108 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like. The terms model and representation can be used interchangeably to refer to any computerized display of a component (e.g., implant, bone, tissue, etc.) of interest.

This system 100 can be used to determine haptic forces based on a virtual tool. Preferably the system 100 determines the haptic forces based on the interaction between the virtual tool and a haptic object. A specific configuration of a prior system having components that determine haptic forces based on a virtual tool is shown in U.S. Patent Appl. Pub. No. 2009/0012532 A1 to Quaid et al., published Jan. 8, 2009, and assigned to MAKO Surgical Corp., which is hereby incorporated herein by reference in its entirety. That prior system and its components could be modified to be used in accordance with the present invention. The present invention, however, differs from the prior system at least in that the present invention determines haptic forces in a new and advantageous way not contemplated in the prior system. In particular, the present determines the interaction between the virtual tool and the haptic object using multiple HIGPs for the virtual tool, identifying subsets of the HIGPs, and determining haptic forces in subspaces corresponding to those subsets. Those haptic forces may then be used to determine a total haptic interaction force. A more detailed explanation of the process of determining those haptic forces is provided in the examples below.

Virtual Tool with Haptic Interaction Geometric Primitives (HIGPs)

Figure 3:
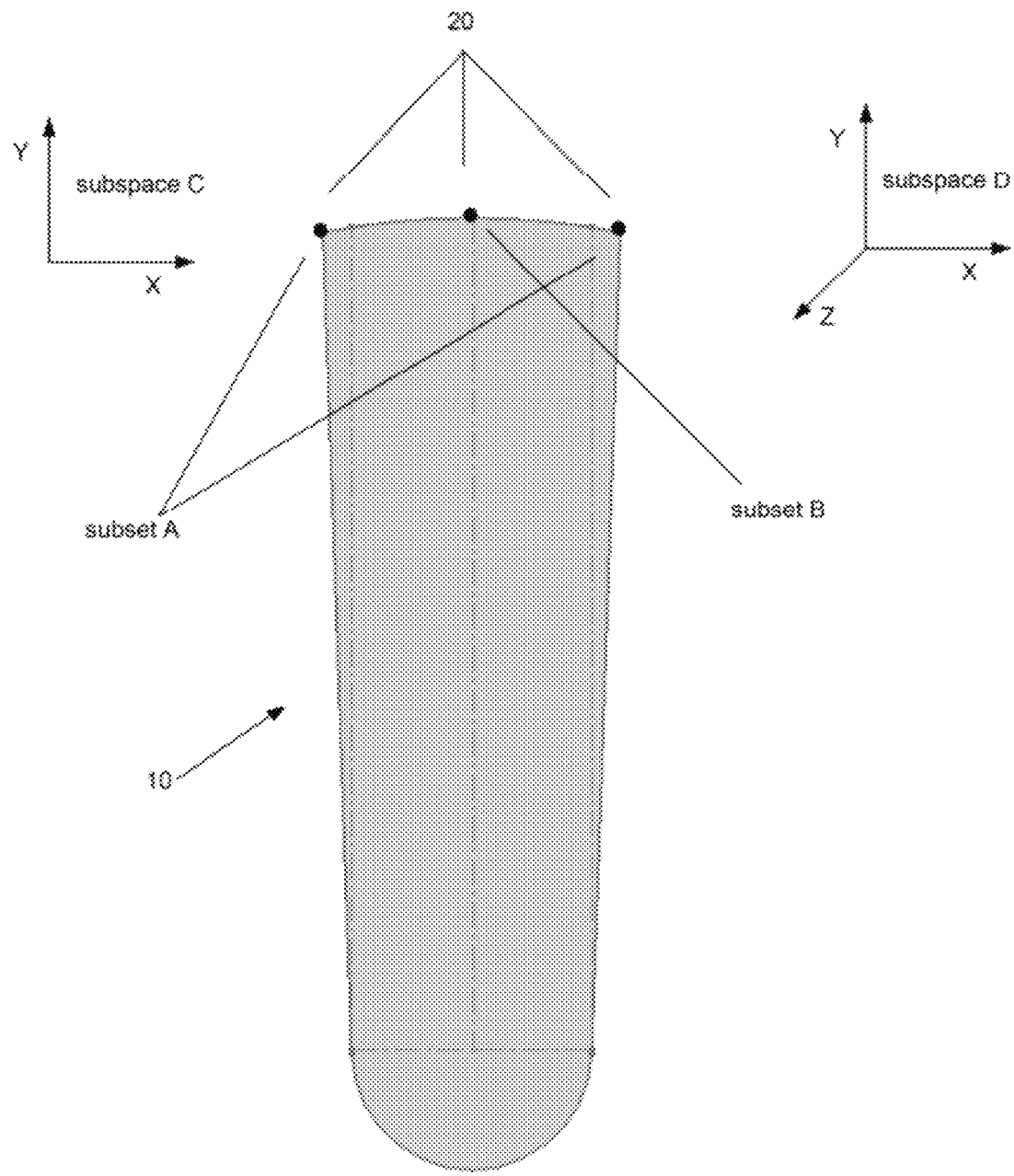
FIG. 3 shows a virtual tool with subsets of haptic interaction points according to an embodiment of the present invention.
Figure 4:
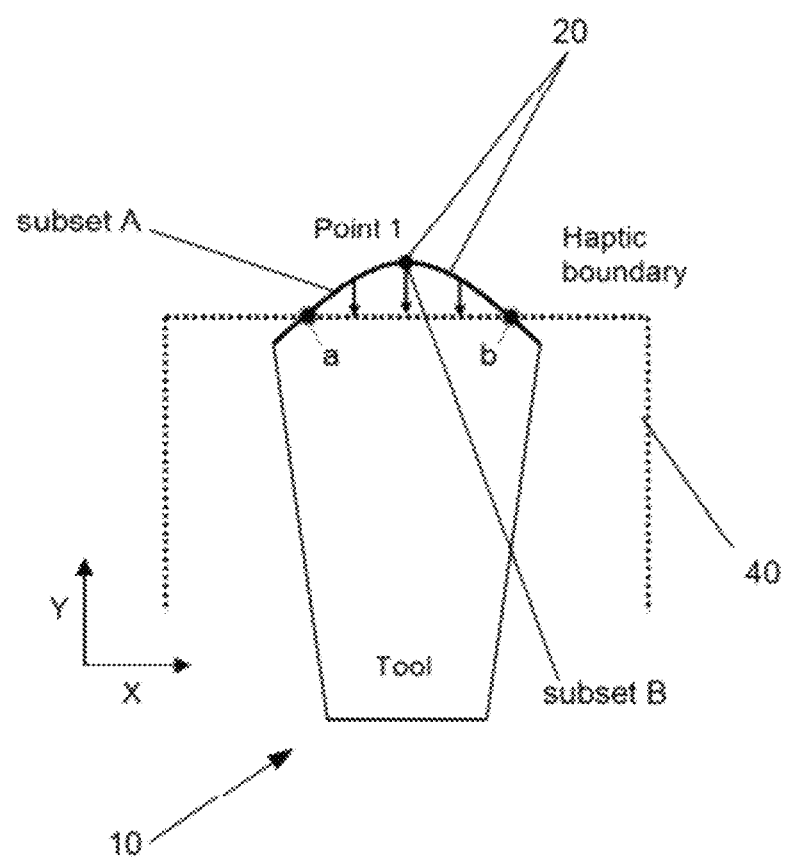
FIG. 4 shows a virtual tool with a haptic interaction arc segment and point according to an embodiment of the present invention.

FIGS. 3 and 4 show an example of an effective area of movement of a virtual tool 10. The virtual tool 10 may represent an object (e.g., surgical tool) in a virtual environment. For example, the virtual tool 10 may represent the manipulation of a physical tool by a user, (e.g., surgeon) to perform a procedure on a patient, such as cutting a surface of a bone in preparation for installing an implant. As the surgeon manipulates the physical tool, the interaction of the virtual tool 10 with a haptic object (not shown) may guide or limit the surgeon by providing haptic (tactile or force) feedback that constrains the physical tool.

Figure 2:
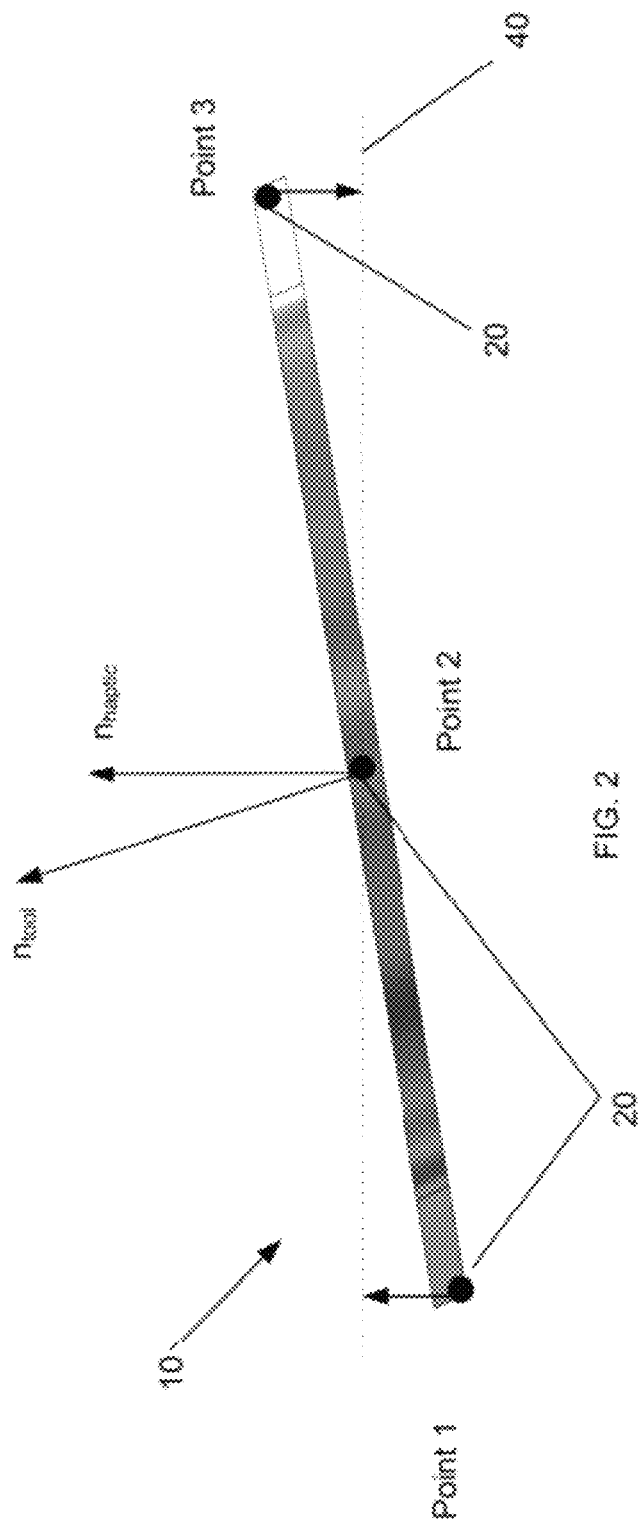
FIG. 2 shows a virtual tool interacting with a boundary of a haptic object.

As shown in FIGS. 2, 3 and 4, the virtual tool 10 may have one or more haptic interaction geometric primitives (HIGPs) 20. The HIGPs 20 may correspond to a location on the virtual tool 10 (e.g., a tip of the virtual tool 10). A geometric primitive may be, for example, any one of a point, line, line segment, plane, circle, ellipse, triangle, polygon or curved arc segment. For example, FIGS. 2 and 3 show a virtual tool 10 wherein the HIGPs 20 are points. Alternatively, FIG. 4 shows a virtual tool 10 wherein the HIGPs 20 are an arc segment and a point.

The computer 102 can determine the interaction of the HIGPs 20 of the virtual tool 10 with one or more boundaries of haptic object(s) in a virtual environment. Boundaries 40 of haptic objects are shown, for example, in FIGS. 2 and 4. A haptic object may be a representation of a pre-defined boundary or component. For example, in the computer-assisted system 100, a pre-operative surgical plan may be used to generate a region for bone resection, and a haptic object may be used to constrain the virtual tool 10 to stay inside boundaries 40 of the haptic object that correspond to the boundaries of the bone-resection region. Accordingly, resulting haptic forces are generated to guide a surgeon according to his/her pre-operative plan.

As stated above, when haptic forces are determined from multiple HIGPs 20, competing forces may cause instability. For a given virtual tool 10, the system 100 of the present invention is configured to provide substantially stable haptics by identifying subsets of the HIGPs and determining haptic forces in subspaces corresponding to those subsets, as described in further detail below.

Embodiment Using Points as HIGPs

Figure 5:
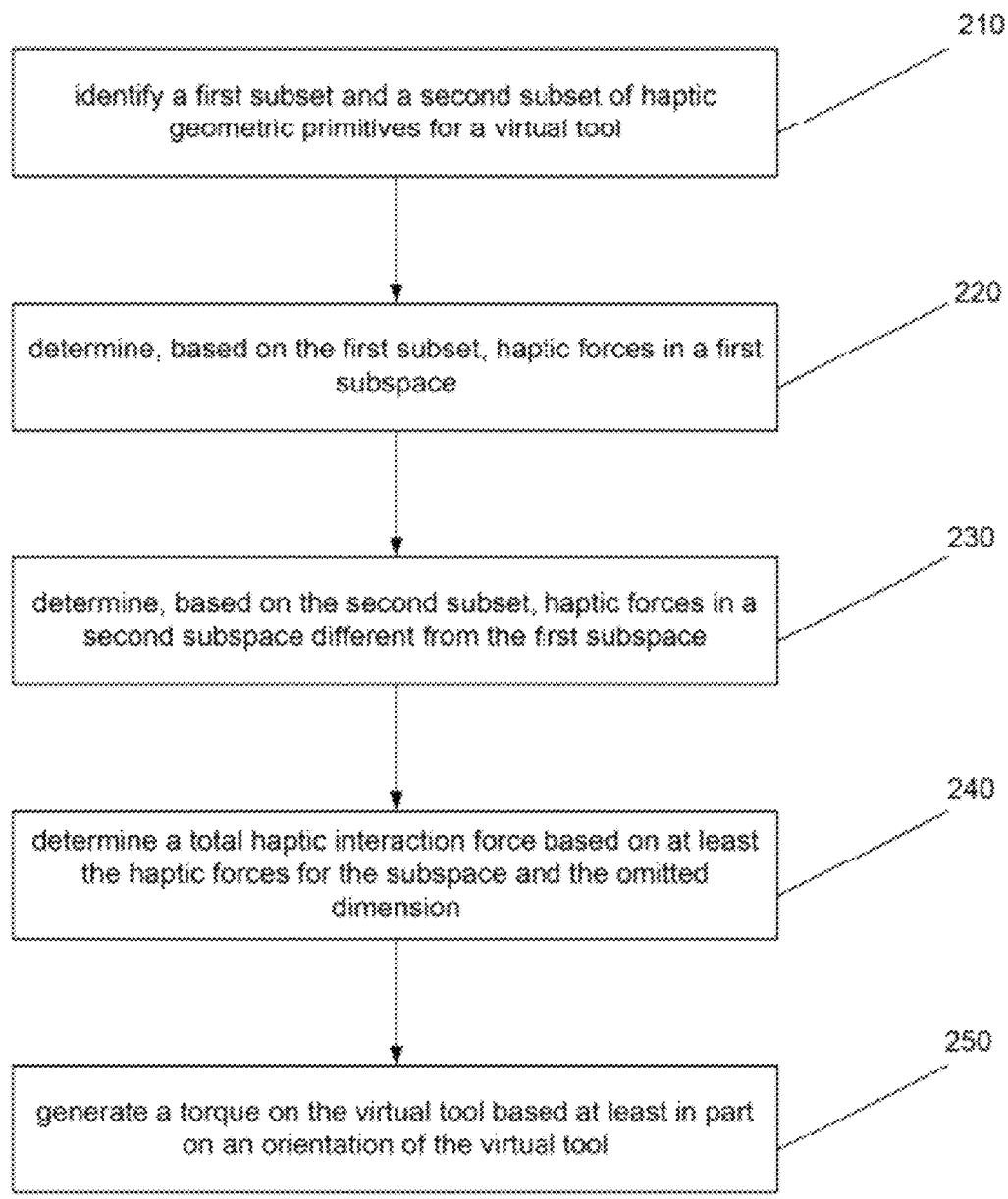
FIG. 5 is a flow chart for a method for providing substantially stable haptics according to the present invention.

With reference to FIGS. 2, 3 and 5, an embodiment of a process for providing substantially stable haptics that can be executed by the system 100 will now be described. In this embodiment, the HIGPs 20 for a virtual tool 10 are all points. These HIGPs 20, in the form of points, will be referred to herein as haptic interaction points (HIPs). A plurality of these HIPs 20 may be, for example, disposed along an outer edge of the virtual tool 10. As shown in FIG. 3, HIPs 20 are located along a top edge of the virtual tool 10.

In step 210 of FIG. 5, subsets of HIPs 20 for a virtual tool 10 are identified. FIG. 3 shows a first subset A and a second subset B. The first subset A preferably includes a plurality of HIPs 20. The second subset B preferably includes only one HIP 20, though it may include more. As shown in FIG. 3, the HIP 20 of the second subset B is disposed between HIPs 20 of the first subset A.

In step 220, haptic forces are determined based on the interaction of the first subset A of HIPs 20 with a boundary 40 of a haptic object. The haptic forces are determined in a first subspace that omits at least one dimension. Preferably, as shown in FIG. 3, in a three-dimensional coordinate system $R^3$, the first subspace C is defined in two dimensions $\{x, y\}$ with the third dimension $\{z\}$ being omitted. Haptic forces from HIPs 20 of subset A may be mapped to a subspace C of the special Euclidean group SE(3). Each force acting on HIPs 20 of subset A may be mapped to subspace C using a projection matrix, which is akin to a spatial filter. For example, the projection matrix that maps the force $[f_x, f_y, f_z]^T$ in three-dimensional space $R^3$ to the force $[f_x, f_y, 0]^T$ can be described as $$P = \begin{bmatrix} 1 & 0 & 0 \\ 0 & 1 & 0 \\ 0 & 0 & 0 \end{bmatrix}, \text{ such that } P \begin{bmatrix} fx \\ fy \\ fz \end{bmatrix} = \begin{bmatrix} fx \\ fy \\ 0 \end{bmatrix}$$

The haptic forces determined from the HIPs 20 in subset A are projected onto subspace C. Accordingly, haptic forces determined from the HIPs 20 of subset A in the x and y dimension are determined and haptic forces from the HIPs 20 of subset A in the z dimension are omitted. Mapping haptic forces from each HIP of the first subset in the first subspace assists in stabilizing a virtual tool with multiple HIGPs by eliminating the unstable nature of competing haptic interaction forces.

In step 230, haptic forces from the second subset B of HIPs 20 are determined in a second subspace different from the first subspace. Preferably, as shown in FIG. 3, in a three-dimensional coordinate system, the second subspace D is defined in three dimensions $\{x, y, z\}$ with the third dimension $\{z\}$ (normal to x, y) being the dimension that was omitted in the first subspace C. Accordingly, the haptic forces for the second subset B of HIPs 20 are defined by forces in three dimensions $\{x, y, z\}$ in the second subspace D. As shown in FIG. 3, the z dimension is normal to the x and y dimension. As a result, haptic forces normal to subspace C (in the z dimension) are only defined based on the HIPs 20 in subset B. In the embodiment shown in FIG. 3, subset B includes a single HIP 20 positioned between HIPs 20 of subset A. Thus, the haptic forces normal to subspace C are only defined from the single center HIP 20. Relying solely on the single HIP 20 of subset B to define forces normal to the first subspace C reduces the amount of competing haptic interaction forces, which in turn increases stability.

In the preferred embodiment discussed above, the first subspace is a two-dimensional subspace of three-dimensional space $R^3$, and the second subspace is a three-dimensional subspace of three-dimensional space $R^3$. However, other subspaces and other n-dimensional spaces may be utilized. Preferably, the first subspace has at least one less dimension than the second subspace. Even more preferably, the first subspace has only one less dimension than the second subspace.

In step 240, a total haptic interaction force is determined, preferably by summing the haptic forces in the first subspace C and the second subspace D. The total haptic interaction force, f, can be a summation of the individual Haptic forces, $f_i$, from each HIP 20 in subset A and subset B, and can be described as:

$$\vec{f} = \sum_{i=1}^{n} P_i \vec{f}_i,$$

where $P_i$ represents the projection matrix for each particular HIP 20.

In step 250, a torque can be generated to provide a further constraint on the orientation of the virtual tool 10 (and thus the physical tool). Preferably, the torque; τ, may be generated from a tool normal ($\vec{n}_{tool}$) and haptic plane normal ($\vec{n}_{haptic}$) (See FIG. 2) to properly constrain the orientation. For example, $$\vec{\tau} = K\, \theta (\vec{n}_{tool} \times \vec{n}_{haptic}) / \|\vec{n}_{tool} \times \vec{n}_{haptic}\|,$$

where K represents the rotational haptic stiffness, and θ is the angular displacement.

In addition to generating a torque there are several strategies for reducing the contribution of forces that enable the resultant force to be stable as described in A. Petersik, B. Pflesser, U. Tiede, K. Höhne and R. Leuwer, "Realistic Haptic Interaction in Volume Sculpting for Surgery Simulation", Lecture Notes in Computer Science, vol. 2673, 2003.

Embodiment Using Complex Body as HIGPs

Alternatively, the HIGPs 20 may include other complex bodies, such as a curved arc segment, or may include a combination of complex bodies and point(s). As shown in FIG. 4, both the arc segment and point (point 1) are located along a top edge of the virtual tool 10. The process for providing substantially stable haptics for a virtual tool as shown in FIG. 4 is the same as described above. Preferably in step 210, the arc segment is identified as the first subset (subset A) and the point is identified as the second subset (subset B) of the geometric primitives 20.

In step 220, the resulting forces for the arc segment (subset A) are then mapped to a first subspace of the special Euclidean group SE(3). Here, haptic forces are defined from the resulting interference between the curved arc segment (subset A) and a boundary 40 of a haptic object. As shown in FIG. 4 specifically, haptic forces are determined from the penetration of a non-uniform virtual tool 10 into a boundary 40 (haptic wall). There are multiple elastic contact theories that may be used to estimate contact forces from this displacement, including Hertzian contact models, elastic half-space models (See N. Ahmadi, L. M. Keer, and T. Mura, "Non-Hertzian contact stress analysis for an elastic half-space normal and sliding contact," Int. J. Solids Structures, vol. 19, no. 4, pp. 357-373, 1983.), and elastic foundation models.

In the elastic foundation model, contact forces are approximated through the assumption that the deformation at one location does not influence deformations at all locations throughout the object. See Y. Bei, and B. J. Fregly, "Multibody dynamic simulation of knee contact mechanics," Medical Engineering & Physics, vol. 26, pp. 777-789, 2004. This contact model comprises-independent springs evenly-distributed across the contact surface, representing a layer of elastic material. Accordingly, the pressure from any spring element on the surface may be written as $$\bar{p} = \frac{(1-v)E}{(1+v)(1-2v)} \frac{\bar{d}}{n},$$

where E is the spring constant of the elastic layer, v is Poisson's ratio, h is the thickness of the layer, and d is the spring deformation. In this model, the spring deformation is defined as the interpenetration of the undeformed contact surfaces in the direction of the midsurface normal. From this result, haptic forces arising from the penetration of an arc segment 20 into a boundary 40 of a haptic object may be determined through integration, such that $$\vec{f}_i = \int_a^b \bar{p}\, dx.$$

In step 230, haptic forces for point 1 (subset B) are determined in a second subspace different from the first subspace. Preferably, the second subspace is normal to the first subspace. As a result, haptic forces normal to the first subspace are only defined based on point 1.

In step 240, the total haptic force on the virtual tool 10 can be defined from a summation of the individual components projected into the first subspace and second subspace, such that $$\vec{f} = \sum_{i=1}^{n} P_i \vec{f}_i,$$

where $f_i$ represents the contribution of forces from a particular arc segment, point, or surface. For example, the force $f_1$ may be defined from the penetration of the arc segment in the first subspace, and the force $f_2$ may be defined from the penetration of point 1 in the second subspace, normal to the first subspace.

In step 250, a torque is determined to further constrain the orientation of the virtual tool 10. Preferably, the torque may be generated from a tool normal ($\vec{n}_{tool}$) and haptic plane normal ($\vec{n}_{haptic}$) (See FIG. 2) to properly constrain the orientation of the tool. For example, $$\vec{\tau} = K\,\theta(\vec{n}_{tool} \times \vec{n}_{haptic})/\|\vec{n}_{tool} \times \vec{n}_{haptic}\|,$$

where K represents the rotational haptic stiffness, and θ is the angular displacement.

Conclusion

The present invention is not limited to the embodiments disclosed above. Those embodiments, however, disclose examples of configurations that can advantageously provide substantially stable haptics by using a computer to identify multiple HIGPs for a virtual tool, identify subsets of the HIGPs, and determine haptic forces in subspaces corresponding to those subsets. Those haptic forces may then be used to determine a total haptic interaction force. Embodiments can be constructed to overcome the instability problems of prior haptic systems. The present invention can be implemented in a wide variety of configurations beyond those disclosed herein.

For example, the above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network).

The system can include clients and servers. A client and a server are generally remote from each other and typically interact through a communication network. The relationship of client and server arises by virtue of computer programs running on the respective computers and having a client-server relationship to each other.

Communication networks can include, for example, the Internet, a carrier internet protocol (IP) network (e.g., local area network (LAN), wide area network (WAN), campus area network (CAN), metropolitan area network (MAN), home area network (RAN)), a private IP network, an IP private branch exchange (IPBX), a wireless network (e.g., radio access network (RAN), 802.11 network, 802.16 network, general packet radio service (GPRS) network, Hiper-LAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft™ Internet Explorer™ available from Microsoft Corporation, Mozilla™ Firefox available from Mozilla Corporation). The mobile computing device includes, for example, a personal digital assistant (PDA).

Other embodiments of the invention will be apparent to those skilled in the art from consideration of the specification and practice of the invention disclosed herein. It is intended that the specification and examples be considered as exemplary only.

What is claimed is:

1. A system for providing substantially stable haptics, comprising:
at least one computer configured to:
identify a first subset and a second subset of haptic interaction geometric primitives associated with a virtual tool;
determine based on the first subset, haptic forces in a first subspace;
determine based on the second subset, haptic forces in a second subspace having at least one additional dimension to first subspace;
wherein haptic forces in the additional dimension are only determined based on the second subset of haptic interaction geometric primitives, which is different than the first subset of haptic interaction geometric primitives; and
determine a torque to constrain an orientation of the virtual tool, wherein determining the torque comprises defining a virtual tool normal and a haptic plane normal and using the virtual tool normal and haptic plane normal to calculate the torque.

2. The system of claim 1, wherein the first subspace has only one less dimension than the second subspace.

3. The system of claim 1, wherein the first subspace is a two-dimensional subspace of three-dimensional space $R^3$, and the second subspace is a three-dimensional subspace of three-dimensional space $R^3$.

4. The system of claim 1, wherein the at least one computer is configured such that a total haptic interaction force is determined by summing at least the haptic forces in the first subspace and the haptic forces in the second subspace.

5. The system of claim 1, wherein the haptic interaction geometric primitives are at least one of a point, line, line segment, plane, circle, ellipse, triangle, polygon and curved arc segment.

6. The system of claim 1, wherein the first subset includes a plurality of haptic interaction points.

7. The system of claim 6, wherein the second subset includes only one haptic interaction point.

8. The system of claim 7, wherein the haptic interaction point of the second subset is disposed between haptic interaction points of the first subset.

9. The system of claim 1, wherein the first subset constitutes a non-linear boundary of the virtual tool.

10. The system of claim 1, wherein the haptic interaction geometric primitives are disposed along an outer edge of the virtual tool.

11. The system of claim 1, wherein the at least one computer is configured to determine a torque based at least in part on an orientation of the virtual tool.

12. The system of claim 1, wherein the virtual tool represents a surgical tool.

13. A method for providing substantially stable haptics, comprising:
identifying a first subset and a second subset of haptic interaction geometric primitives associated with a virtual tool;
determining based on the first subset, by at least one computer, haptic forces in a first subspace;
determining based on the second subset, by at least one computer, haptic forces in a second subspace having at least one additional dimension to the first subspace;

wherein haptic forces in the additional dimension are only determined based on the second subset of haptic interaction geometric primitives, which is different than the first subset of haptic interaction geometric primitives; and determining a torque to constrain an orientation of the virtual tool, wherein determining the torque comprises defining a virtual tool normal and a haptic plane normal and using the virtual tool normal and haptic plane normal to calculate the torque.

14. The method of claim 13, wherein the first subspace has only one less dimension than the second subspace.

15. The method of claim 13, wherein the first subspace is a two-dimensional subspace of three-dimensional space $R^3$, and the second subspace is a three-dimensional subspace of three-dimensional space $R^3$.

16. The method of claim 13, further comprising:
determining, by at least one computer, a total haptic interaction force by summing at least the haptic forces in the first subspace and the haptic forces in the second subspace.

17. The method of claim 13, wherein the haptic interaction geometric primitives are at least one of a point, line, line segment, plane, circle, ellipse, triangle, polygon and curved arc segment.

18. The method of claim 13, wherein the first subset includes a plurality of haptic interaction points.

19. The method of claim 13, wherein the second subset includes only one haptic interaction point.

20. The method of claim 19, wherein the haptic interaction point of the second subset is disposed between haptic interaction points of the first subset.

21. The method of claim 13, wherein the first subset constitutes a non-linear boundary of the virtual tool.

22. The method of claim 13, wherein the haptic interaction geometric primitives are disposed along an outer edge of the virtual tool.

23. The method of claim 13, further comprising:
determining a torque based at least in part on an orientation of the virtual tool.

24. The method of claim 13, wherein the virtual tool represents a surgical tool.

* * * * *